United States Patent [19]

Deutsch et al.

[11] Patent Number: 4,522,923

[45] Date of Patent: Jun. 11, 1985

[54] SELF-CONTAINED ASSAY METHOD AND KIT

[75] Inventors: Alice Deutsch, New York; Herbert Platt, Great Neck, both of N.Y.

[73] Assignee: Genetic Diagnostics Corporation, Great Neck, N.Y.

[21] Appl. No.: 538,692

[22] Filed: Oct. 3, 1983

[51] Int. Cl.³ .................... G01N 33/52; G01N 33/54; B65D 71/00

[52] U.S. Cl. .................... 436/536; 422/57; 422/58; 422/59; 422/60; 422/61; 436/537; 436/538; 436/539; 436/540; 436/541; 436/542; 435/7

[58] Field of Search .................... 422/57-61, 422/102; 436/536-542, 800, 807, 808, 818; 435/7

[56] References Cited

U.S. PATENT DOCUMENTS 3,706,305 12/1972 Berger et al. .................... 422/102
4,301,139 11/1981 Feingers et al. .................... 422/61
4,424,279 1/1984 Bohn et al. .................... 422/61
4,458,020 7/1984 Bohn et al. .................... 422/61

FOREIGN PATENT DOCUMENTS 2028822 12/1971 Fed. Rep. of Germany ...... 422/102
2449894 9/1980 France .................... 422/61
28648 2/1984 Japan .................... 422/61

*Primary Examiner*—Christine M. Nucker
*Attorney, Agent, or Firm*—Sprung Horn Kramer & Woods

[57] ABSTRACT

The present invention describes an apparatus and method for conducting immunochemical reactions in a self-contained sealed unit that requires only the addition of an unknown sample and water. The apparatus comprises a test tube with at least three chambers each containing different chemicals, including a solid sphere, and separated from each other by a water-soluble barrier.

13 Claims, 3 Drawing Figures

SELF-CONTAINED ASSAY METHOD AND KIT

The present invention relates to a simplified method and apparatus for conducting immunochemical reactions.

BACKGROUND OF THE INVENTION

Although there are now many assay methods available for measuring hormones and other substances in serum or urine, most of these methods involve complicated manipulations. Those methods using enzyme immunoassay could be suitable for a physician's office or the home because they are non-isotopic, but they require too high a level of technical expertise. This is one of the reasons the home test kit for pregnancy diagnosis, for example, is not as accurate as it could be.

It is accordingly an object of the present invention to provide an assay system that is safe and accurate even when used by an individual who is not technically trained.

These and other objects and advantages are realized in accordance with the present invention pursuant to which there is provided a container subdivided into at least three chambers separated from one another by at least first and second water-soluble barriers and each containing a different substance. By introducing a water-containing reactant into the first chamber the reactant will be held in contact with the first chamber contents for a predetermined length of time, controlled by the rate of dissolution of the first barrier and the amount of water in the sample. When the first barrier is ruptured, liquid from the first chamber mixes with the contents of the second chamber. Again after a predetermined time interval, the second barrier is ruptured and eventually material from the second chamber mixes with the contents of the final chamber. The barrier between the second and final chambers may be pervious to liquid but not solids so the rupture permits passage of liquid but not solids. One could use the solid or the liquid for assay but it is more convenient to use the liquid. Advantageously it mixes with a liquid already contained in the final chamber which can additionally contain a solid. Alternatively liquid is added to the final chamber at a suitable stage in the process.

In accordance with another aspect of the invention, the third chamber is subdivided into two compartments and the barrier between the second and third chambers has two sections which are differently breached. Thus, when the barrier is first attacked the liquid from the second chamber will drain into the first compartment and, subsequently the solid from the second will fall into the second compartment. Liquid will either already be in the second compartment or will be added thereto, and then an assay will be run. Advantageously, this will be colorimetric.

It would be advantageous if liquid is in the third chamber from the outset but in such event it is necessary that the liquid not produce rupture of the barrier prior to use. This can be accomplished by using liquids which will not attack the barrier under normal conditions but only when properly triggered, e.g., the liquid can be neutral but the barriers will be breached only by alkali so alkali is introduced into the first compartment along with the sample or dry alkali is present in the first compartment, becoming active for successive breaching of the barriers only when liquid is introduced into the first compartment.

In this way the contents of the second and subsequent chambers are never touched by the operator.

Advantageously the container is a test-tube with vertically stacked chambers separated by the water-soluble barriers and provided with a removable cap so that the test specimen can be added to the first chamber. The cap is replaced, the tube shaken and left to stand, the process proceeding as outlined.

The several water-soluble barriers can be the same or different, depending upon the contents of the chambers and the desired rate of dissolution. Similarly their physical constitution can vary from a continuous plastic-like self-supporting film or sheet to a porous support coated with a water-soluble film-forming material to a self-supporting film on a support having holes of a size such that, upon rupture of the water-soluble barrier, solids within the chamber but not liquids will be held back, i.e. filtered out, when material advances to the next chamber.

Suitable water-soluble barriers are formed of polyvinyl alcohol acetalized or esterified if desired to control its water-solubility. Cellulose ethers such as methyl cellulose, carboxymethylcellulose and the like can also be used, as can vegetable gums such as agar, Irish moss, guar, alginates, and the like. They can be selected and/or pretreated so as to become soluble in dependence upon a pH change, e.g. release of alkali such as NaOH or cation exchange to replace calcium by sodium could result in a Na-containing liquid which would dissolve a water-insoluble calcium alginate film.

As stated, the film-formers could merely be coated on an insoluble support such as a woven or non-woven fabric. The fabric interstices can be of such size as to filter out solids such as ion exchange particles as liquid flows downwardly to the next chamber.

The chambers can be loaded from the bottom up, i.e. load the third chamber (one or two compartments), place the second barrier, load the second chamber, place the first barrier, load the first chamber and then cap the test tube. Alternatively both barriers can first be placed and then the chambers loaded as by a hypodermic syringe, although there will necessarily be small holes in the barriers produced by loading the chambers. This is permissible where such small holes are not important or where they might become quickly sealed-over because of their composition or the composition of the material within a particular chamber. Another possibility is to pre-load the chambers as plastic containers and then stack the containers in a test tube.

The barriers can be held in place by an adhesive, by wax, thermoplastically if appropriate, or any other means. The cap can be a friction fit or a screwed cap or it too can be a plastic film, although it should not be water-soluble. The sample can be loaded into the first chamber by removal of the cap or by penetration as with a hypodermic syringe. If the cap is no longer present, a finger over the top of the tube will still permit shaking while preventing loss of ingredients.

More than two barriers and three chambers can be present, if desired. Advantageously they each dissolve or are breached in about 1 to 30, preferably about 2 to 10, minutes.

The contents of the individual chambers can vary widely being liquid or solid or both and they may fill each chamber or more usually, especially in the second and third chambers, occupy only a portion of the space so as to permit entry of all the material desired from the immediately preceding chamber.

Suitable materials include antigens, antibodies or conjugated antigens and antibodies alone or immobilized on supports and/or filters, alkalis, acids and the like.

The invention will be further described with reference to the accompanying drawing wherein.

Figure 1:
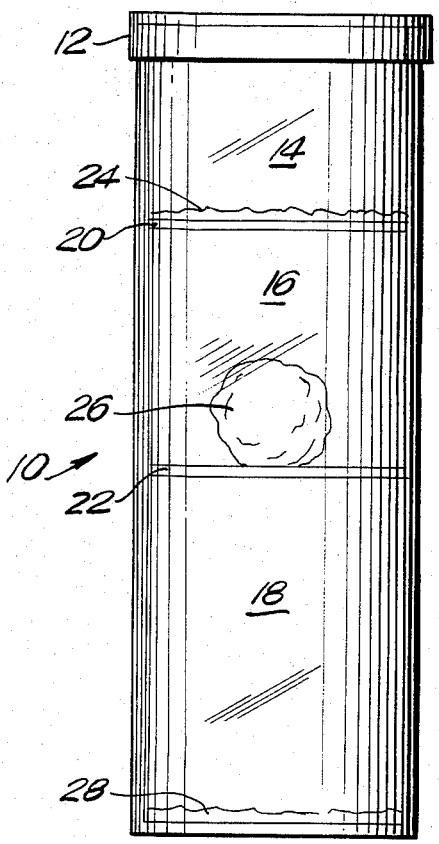
FIG. 1 is a diagrammatic sketch of a capped test tube in accordance with one embodiment of the invention.

Referring now more particularly to FIG. 1, there is shown a test tube 10 provided with a removable cap 12. The test tube is subdivided into three vertical chambers 14, 16 and 18 by first and second horizontal barriers 20 and 22. The barriers are water-soluble in whole or in part, i.e. they may be water-soluble films on an insoluble screen so that when the water-soluble material dissolves the screen will filter out solids but permit the passage of liquid.

Within each chamber 14, 16, and 18, there are shown to be solid reagents 24, 26 and 28, respectively, although they could be liquid so long as they would not attack the barriers, e.g. if they contain no water.

In use, cap 12 is removed, an aqueous sample such as urine or blood is added to chamber 14, cap 12 is replaced, the tube is shaken and then left to stand in vertical position. After a predetermined time to allow reaction in the chambers as a result of progressive breaching of the barriers, the color in chamber 18 will indicate the presence or absence of a particular material in the sample.

If desired, the contents of chamber 18 can be read by an instrument, using ordinary light, ultraviolet light, infrared radiation, or the like. This may give a quantitative analysis of the sample rather than merely qualitative.

Figure 2:
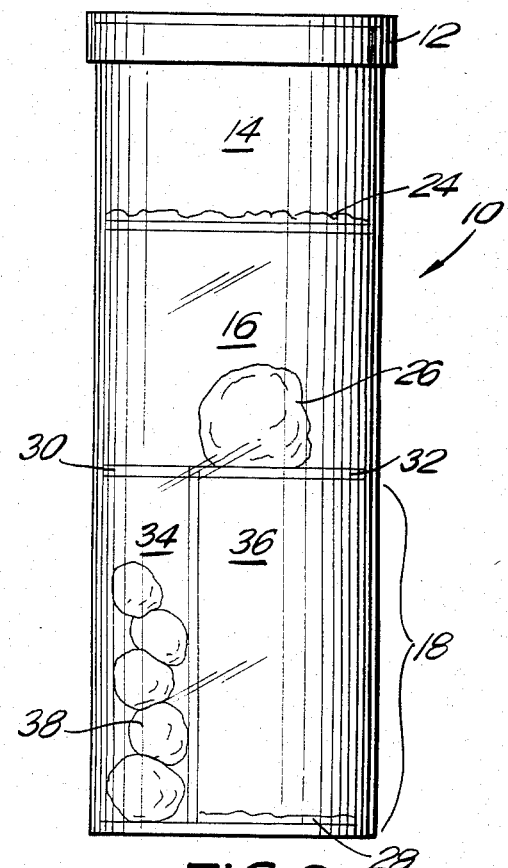
FIG. 2 is a lateral elevation of another embodiment of the invention.

In FIG. 2, the barrier 22 is made up of two sections 30 and 32, respectively, overlying compartments 34 and 36 into which the third chamber 18 is subdivided. A solid absorbent 38 is contained in compartment 34 and a liquid in compartment 36. Barrier section 30 is first breached whereupon the liquid in second chamber 16 drains into compartment 34. The wet solid 26 then later falls into compartment 36 when barrier section 32 is ultimately breached. Solid 26 mixes with the contents of compartment 36 and the liquid in compartment 36 is colorimetrically determined as the assay of the original sample.

Figure 3:
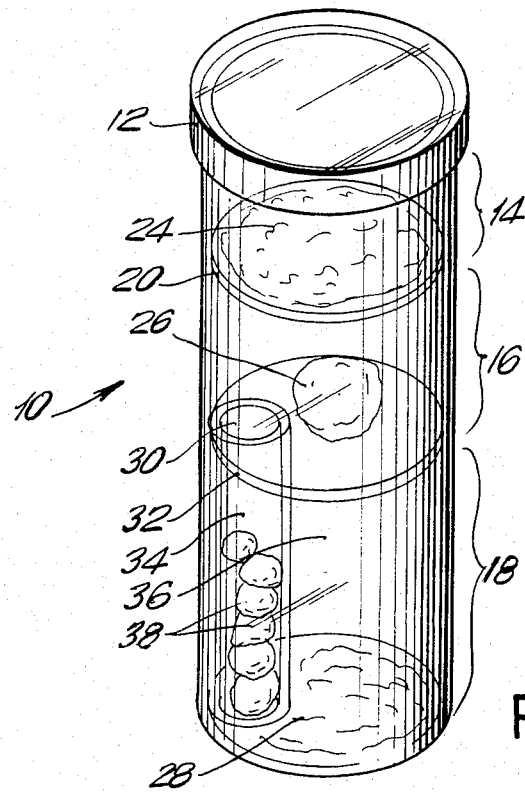
FIG. 3 is a perspective view of the embodiment of FIG. 2, with some of the contents removed for ease of understanding.

In FIG. 3 the structure of FIG. 2 is seen diagrammatically with only some of the contents but all of the structural elements.

An illustrative sequence utilizing the device of FIGS. 2 and 3 is as follows:

(1) The device is uncapped.
(2) A dropper full of water is added to the first chamber.
(3) A dropper full of sample is also added to the first chamber.
(4) The device is capped and gently shaken and set upright.
(5) After less than 1 minute, the liquids in the first chamber break through the barrier and fall into the second chamber.
(6) Now the solid sphere and the liquids incubate together. After 20 to 30 minutes the liquid in the second chamber falls into the narrow compartment of the third chamber after the barrier dissolves. This liquid is absorbed.
(7) Then after about 5 minutes the barrier fully dissolves and the sphere in the second chamber falls through, into the second compartment of the third chamber.
(8) When this happens, the device is uncapped by the user.
(9) The user adds a dropperful of water to the second compartment.
(10) The device is recapped and shaken gently and then set upright.
(11) Color should develop in 5 minutes.

As noted, the second compartment of the third chamber may contain liquid from the outset in which event steps 8, 9 and 10 will not be necessary.

The invention will be further described in the following illustrative examples with reference to the drawing.

EXAMPLE 1

A device was constructed using a 10×75 mm test tube. Part of a 3 cc syringe was cut up to make a 1 cm high cylinder. One ml of the substrate paranitrophenyl phosphate (1 mg/ml in 10% diethanolamine, pH 9.8) was pipetted into each test tube. Then parafilm was placed over one end of the cutoff syringe cylinders and this was forced into the end of the test tube thereby forming a barrier.

Next, a polystyrene sphere previously coated with a digoxin antibody, was placed into the top chamber so that it rested on the parafilm. Over the sphere was pipetted 300 µl of 1% bovine serum albumin in phosphate buffered saline (PBS).

Then 50 µl of 100 µg/ml digoxin and 50 µl 1:5 dilution of digoxin-alkaline phosphatase (purchased from Immunotech) were added to the bead. PBS was used as a control for the digoxin. Each sphere was incubated 10 minutes at 37° C.

The liquid that the sphere was sitting in was decanted. The parafilm barrier that the sphere was resting on was punctured with a needle. The sphere fell through the barrier to the substrate solution below. After 5 and 10 minutes at room temperature the optical density of each solution was measured.

|  | O.D.* | O.D.** |
|---|---|---|
| sphere incubated with digoxin | .225 | .276 |
| sphere incubated with no digoxin | .661 | .962 |

*After 5 min.
**After 10 min.

EXAMPLE 2

In this variation, substance 24 is an antibody conjugated to an enzyme. Substance 26 is an antigen immobilized on a polystyrene sphere. Substance 28 is a lyophilized enzyme substrate.

To use, a 0.5 ml liquid containing the material to be measured, for example dilantin, is introduced into the top chamber. The test tube apparatus is recapped, gently shaken, and left standing upright. This causes rehydration and mixing of dilantin-specific antibody conjugated to enzyme. This also incubates for 10 minutes. At the end of this time, the barrier dissolves and antibody-enzyme+dilantin flow into the middle chamber containing the sphere. Any antibody-enzyme not bound to sample dilantin will now bind to the dilantin on the sphere. After about 5 minutes the barrier is dissolved. The liquid now contains antibody-enzyme-dilantin and it passes into the compartment 34 where it is absorbed. After 2 minutes the sphere drops into compartment 36. The user adds 1 ml $H_2O$. This rehydrates the material 28 which is a substrate for the enzyme conjugated to the antibody. After 5 minutes a color develops. This indicates that the sample contains no dilantin. If there was no color after 5 minutes, it would indicate that the unknown sample contains dilantin.

It will be understood that the specification and examples are illustrative but not limitative of the present invention and that other embodiments within the spirit and scope of the invention will suggest themselves to those skilled in the art.

What is claimed is:

1. A test device comprising a container, at least two water-soluble barriers subdividing said container into at least three superposed chambers, and different biologically active substances in each chamber, whereby upon introduction of an aqueous biological sample to be tested into the topmost chamber the sample will successively mix with the contents of the chambers, the contact time in each chamber being a function of the water solubility of the barriers.

2. A device according to claim 1, wherein each water-soluble barrier permits passage of an aqueous sample therethrough in from about 1 to 30 minutes.

3. A device according to claim 1, wherein each water-soluble barrier permits passage of an aqueous sample therethrough in from about 2 to 10 minutes.

4. A device according to claim 1, wherein the container is a transparent cylinder.

5. A device according to claim 4, including a removable replaceable cap.

6. A device according to claim 1, wherein at least one of the chambers contains an antigen, an antibody, an enzyme or a conjugate thereof.

7. A device according to claim 1, wherein at least one of the chambers contains an antibody directed against human chorionic gonatotropin hormone.

8. A device according to claim 1, wherein the lowermost chamber is subdivided into first and second compartments and is surmounted by a barrier having first and second sections of differing solubility respectively overlying the first and second compartments, the second chamber containing a solid, whereby the liquid in the second chamber breaches the first section of the barrier and falls into the first compartment, the wet solid in the second chamber thereafter breaching the second section and falling into the second compartment.

9. A device according to claim 8, including a liquid in the second compartment which does not attack its covering barrier.

10. A method of testing an aqueous biological sample for the presence therein of a particular material which comprises providing a test device according to claim 1, the biologically active substances in each chamber being so chosen that the color or absence of color in the final chamber indicates the presence or absence of the particular material in the initial sample, adding the sample to the topmost chamber, and allowing the device to stand in vertical position for a time sufficient for the color change to take place if it will.

11. A method according to claim 10 wherein the container is a transparent cylinder with a replaceable cap, after the sample has been added to the topmost chamber the cap being replaced and the container shaken.

12. A method according to claim 10, wherein at least one of the chambers contains an antigen, an antibody, an enzyme or a conjugate thereof.

13. A method according to claim 10, wherein at least one of the chambers contains an antibody directed against human chorionic gonatotropin hormone.

* * * * *